United States Patent [19]

Tamura et al.

[11] Patent Number: 4,718,576
[45] Date of Patent: Jan. 12, 1988

[54] FLUID INFUSION PUMPING APPARATUS

[75] Inventors: Paul S. Tamura; Ted A. Hadley, both of Mountain View, Calif.; Wayne R. Kelsey, Des Plaines, Ill.

[73] Assignee: Oximetrix, Inc., Mountain View, Calif.

[21] Appl. No.: 812,620

[22] Filed: Dec. 23, 1985

[51] Int. Cl.[4] .................. B67D 5/08; A61M 37/00
[52] U.S. Cl. ........................................ 222/63; 222/333; 604/67; 604/153
[58] Field of Search ............... 222/63, 333, 36, 37, 222/639; 604/152, 153, 67

[56] References Cited

U.S. PATENT DOCUMENTS

| | | | |
|---|---|---|---|
| 3,809,871 | 5/1974 | Howard et al. | 604/49 X |
| 3,985,133 | 10/1976 | Jenkins et al. | |
| 4,037,598 | 7/1977 | Georgi | |
| 4,126,132 | 11/1978 | Portner et al. | |
| 4,217,993 | 8/1980 | Jess et al. | |
| 4,280,494 | 7/1981 | Cosgrove et al. | |
| 4,308,866 | 1/1982 | Jelliffe | |
| 4,393,849 | 7/1983 | Petre et al. | |
| 4,396,385 | 8/1983 | Kelly et al. | |
| 4,443,216 | 4/1984 | Chappell | |
| 4,451,255 | 5/1984 | Bujan et al. | 604/153 X |
| 4,474,309 | 10/1984 | Solomon | 222/333 X |
| 4,475,666 | 10/1984 | Bilbrey et al. | 604/152 X |
| 4,482,346 | 11/1984 | Reinicke | 604/152 |
| 4,526,515 | 7/1985 | DeVries et al. | 604/153 X |

Primary Examiner—Joseph J. Rolla
Assistant Examiner—Gregory L. Huson
Attorney, Agent, or Firm—Martin L. Katz; Robert W. Stevenson; Michael J. Roth

[57] ABSTRACT

A fluid infusion positive displacement pump includes a plunger driven by a stepping motor which is operated by a motor control system. The control system advances the plunger to expel liquid in a series of incremental steps at a user-set pumping rate and until a preset total dosage has been delivered with the pumping rate being determined by the waiting time between each step. In order to minimize shock to the patient, the pump is operated at a plurality of increasing fractional rates during the start of pumping and at a plurality of decreasing fractional rates at the termination of pumping with the user-set (maximum) pumping rate occurring between such fractional rate pumping periods.

13 Claims, 6 Drawing Figures fig_2

FLUID INFUSION PUMPING APPARATUS

BACKGROUND OF THE INVENTION

1. Field of the Invention

This invention relates to apparatus for pumping fluids intravenously or intra arterially to patients, and more particularly, it relates to the control systems for such fluid infusion pumping apparatus which regulate the flow rates under which such pumping is accomplished.

2. Description of the Prior Art

In recent years there has been a considerably increased use of positive displacement fluid infusion pumping devices for delivering fluids intravenously or intra arterially to patients in hospitals or other patient care locations. These have to a large extent replaced the time honored gravity flow control systems primarily due to their much greater accuracy in determining delivery rates and dosages, their relative sophistication in permitting a flexible and controlled feed from multiple liquid sources, and particularly their ability to control with precision the amount of dangerous drugs delivered to a patient over a given period of time.

In a typical positive displacement fluid infusion pump system, stepping motors are used to gradually deliver the I.V. fluids by displacing an amount of liquid trapped within a chamber in very small increments. In this way, shock to the nervous system of a patient is minimized and a relatively uniform flow of fluid is obtained. Various prior United States patents disclosing typical fluid infusion pump control systems include U.S. Pat. Nos. 4,474,309 to Edward G. Solomon; 4,443,216 to Anthony G. Chappell; 4,396,385 to Timothy G. Kelly et al.; 4,392,849 to John H. Petre et al.; 4,308,866 to Roger W. Jelliffe et al.; 4,280,494 to Robert J. Cosgrove, Jr. et al.; 4,217,993 to Thurman S. Jess et al.; 4,126,132 to Peer M. Portner et al.; 4,037,598 to Heinz W. Georgi; and 3,985,133 to John Arthur Jenkins et al.

The United States patent to Solomon, U.S. Pat. No. 4,474,309, discloses a typical fluid infusion pump system wherein a small disposable cassette having a pumping chamber with a flexible diaphragm forming one exterior surface thereof is adapted to be placed in a driver or controller mechanism, and with the cassette including a programmable plunger adapted to interact with the diaphragm to pump fluid from the chamber. The plunger is driven by a stepping motor through a series of short, liquid-displacing steps and then retracted quickly once it has reached its maximum displacement in the chamber so as to assure as uniform a flow of liquid as possible. The inlet and outlet valves to the pumping chamber may be actuated from the driver (as is the case with the inlet valve in the Solomon patent disclosure) or they may be comprised of check valves controlled by the differential pressure provided by the pumping plunger (as in the case with the outlet valve in the Solomon disclosure patent). As is conventional with pumping systems of this type, the user sets a rate at which the fluid is to be delivered as well as the total dosage which is to be delivered by the apparatus. The system will then operate by providing the fluid at the predescribed rate in a generally uniform flow and will automatically shut down when the accumulated running total of liquid delivered equals the preset total dosage to be delivered.

While careful control of the pumping mechanism and limiting the delivery to short strokes spaced over time insures a more uniform flow rate, it has been found that physiological shocks may still occur in particular patients, especially when the delivery of I.V. solutions is started and also when it abruptly stops.

SUMMARY OF THE INVENTION

With the fluid infusion pumping apparatus of the present invention, a special ramping control means is provided for automatically initiating the delivery of the infusion liquid in a phased manner so that liquids are delivered at a series of fractional rates prior to the delivery at the full user set rate with such fractional rates successively increasing up to the time that the pump operates at the preset rate. Also, a phased delivery occurs prior to the stopping of the pump upon the delivery of the full dosage whereby the pump is automatically operated at a plurality of fractional rates with such fractional rates successively decreasing until the pump comes to a complete stop. In this manner, the physiological shock upon the patient at the start and stopping of the infusion is minimized, and the overall delivery of the prescribed dosage is accomplished in a manner best suited to the typical patient's bodily needs.

DESCRIPTION OF THE PREFERRED EMBODIMENT

By way of example, the pumping control system of the present invention is shown as used with an infusion pumping apparatus of the type disclosed and claimed in prior U.S. Pat. No. 4,474,309 to Edward G. Solomon. Reference to this patent may be had for a more complete description of the details of the pumping apparatus, but such details are not particularly relevant to or necessary for an understanding of the present invention.

Figure 1:
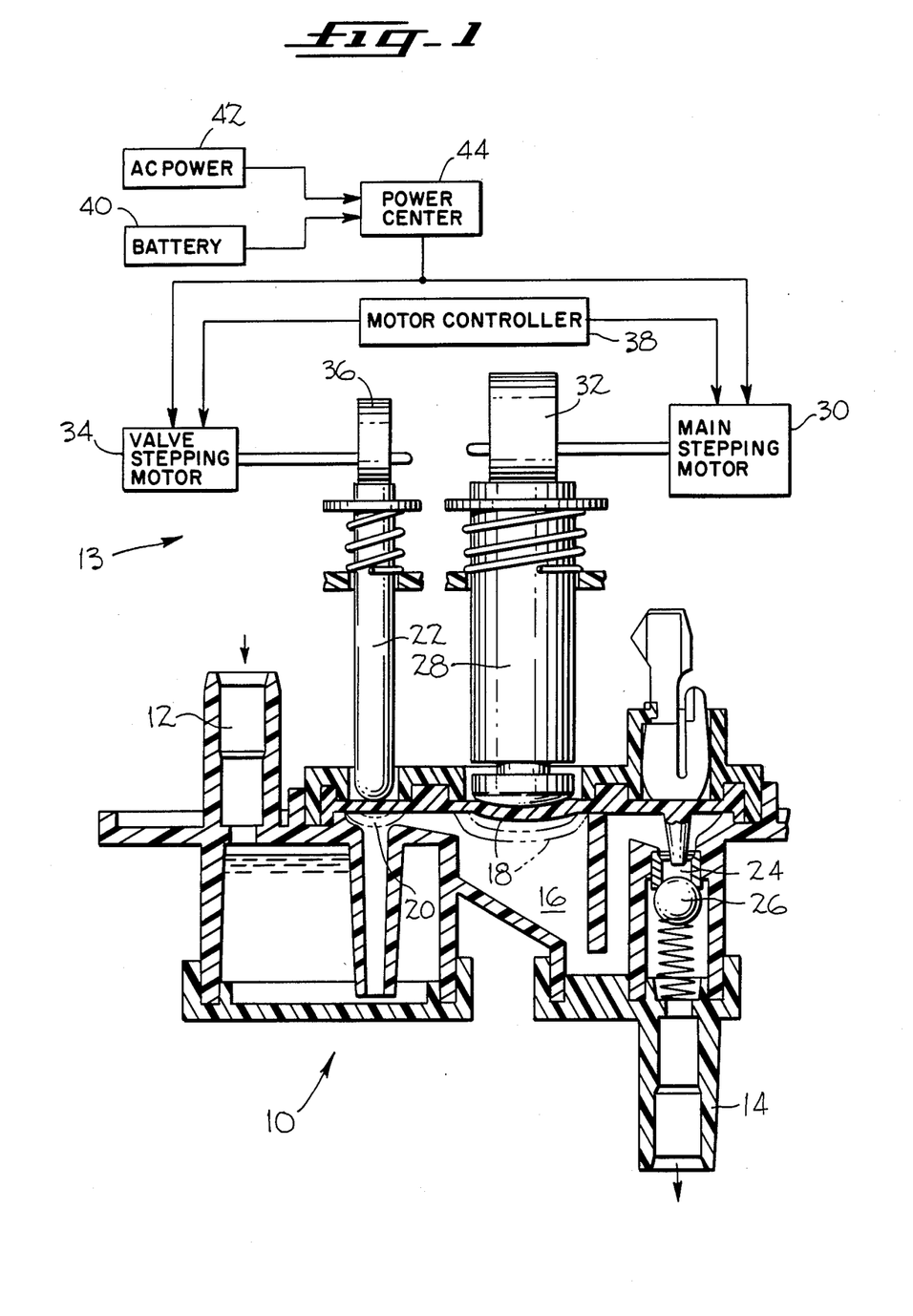
FIG. 1 is a schematic view illustrating in cross-section a fluid infusion pump cassette and the plunger and valving members for controlling the operation thereof and, primarily in block diagram form, the apparatus for controlling the pumping and valving action.

Referring first to FIG. 1, it will be seen that the pumping apparatus of the present invention includes a disposable cassette 10 which is adapted to receive fluid supplied by gravity to an inlet port 12 therein, and, under the control of the pump driver apparatus 13, the cassette is adapted to positively displace fluid out of the outlet port 14, which is arranged to be connected by suitable tubing to the patient to which the fluids are intravenously or intra arterially delivered. Located within the body of the cassette is a pumping chamber 16, the upper wall of which is formed by an exposed flexible diaphragm 18 of elastomeric material. Fluid entry into the pumping chamber is through an inlet port 20 which is controlled by a vertically reciprocatable valve member 22 extending from the driver mechanism 13 and which is arranged to depress a portion of the diaphragm 18 to close off the inlet port (as indicated in phantom line in FIG. 1). Alternatively, a check valve could be used to close off the inlet port, such check valve closing when the chamber pressure exceeds the upstream pressure and opening under the reverse condition (i.e., during chamber refilling). Discharge from the pumping chamber is through an outlet port 24 which is normally closed by a spring loaded ball check valve 26 set to open when the pressure in the pumping chamber rises above a predetermined value, e.g., 5 psi. The displacement of fluid from the pumping chamber 16 is accomplished by means of a plunger 28 extending from and driven by the driver apparatus 13. The plunger is operated in incremental steps depressing the diaphragm 18 to thereby reduce the volume of the pumping chamber to ultimately displace a predetermined volume therefrom (as shown by the phantom line indication in FIG. 1). With the valve member 22 closing the chamber unit during the pumping (downward) movements of plunger 28, the pressure developed within the pumping chamber will open the outlet valve 26 permitting the predetermined volume of fluid to be discharged throughout outlet port 14. As the plunger 28 is then returned to its uppermost position (shown in full lines in FIG. 1), the outlet valve 26 closes to stop the delivery of fluid, and the inlet port 20 will be opened by elevating the valve member 22 so as to permit fluid to enter the pumping chamber to replace the displaced volume. By repeated incremental downward movements of the plunger 28 between the positions illustrated in FIG. 1 and retraction back to the uppermost position, fluid is pumped over a given period of time until a predetermined preset dosage has been delivered.

The pumping plunger 28 is driven in a number of separate incremental steps during each downward pumping stroke by a main stepping motor 30 which rotates a cam 32 against the spring-loaded end of plunger, as shown. The valve member 22 is similarly driven by a valve stepping motor 34 operating a cam 36 against the spring-loaded end of the valve member. Both the main stepping motor 30 and the valve stepping motor 34 are controlled by motor controller circuitry 38 and are arranged to be powered either by a battery 40 or an A.C. power source 42 as determined by a switching power center 44.

Figure 2:
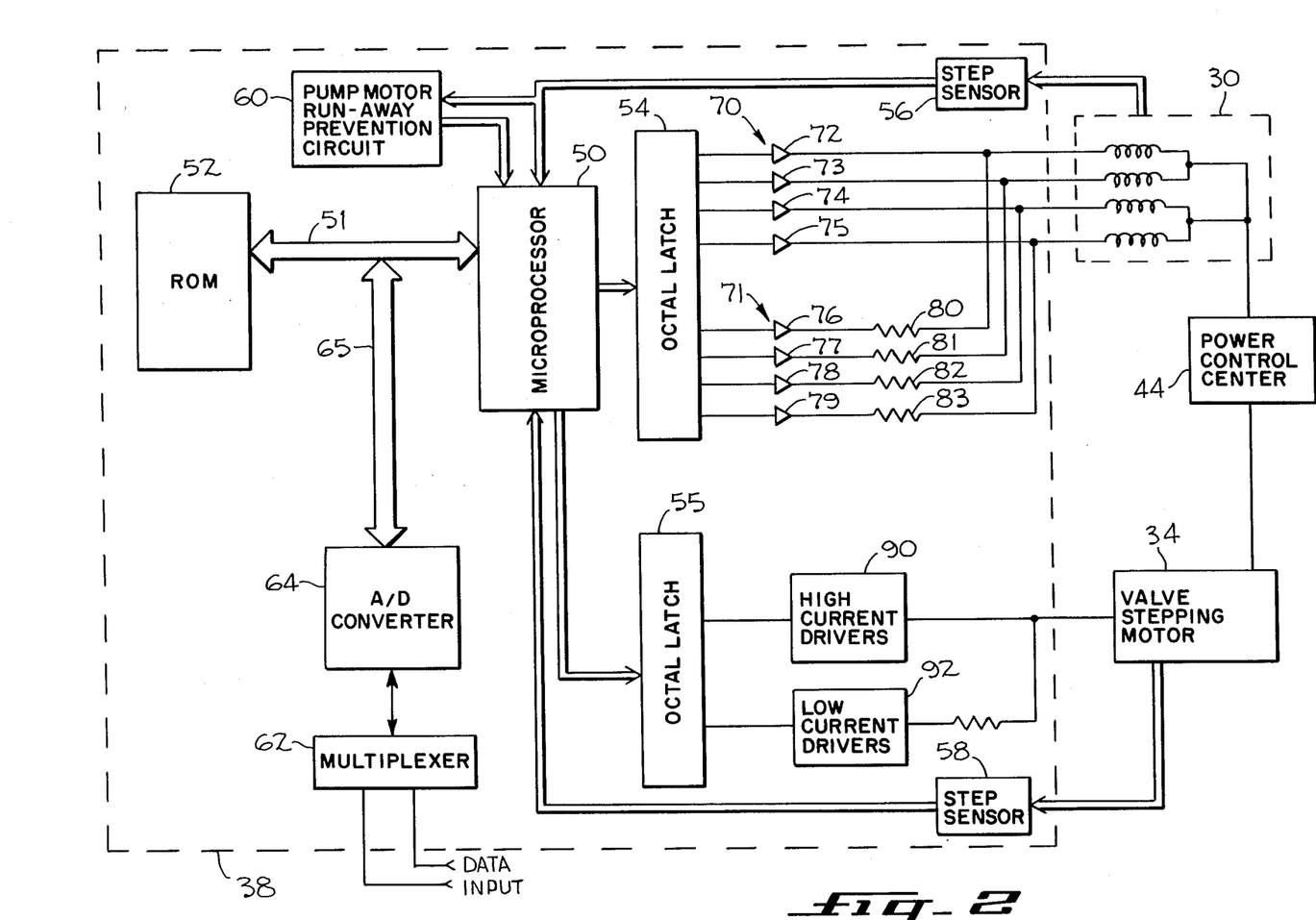
FIG. 2 is a schematic illustration of the motor controller for the infusion pumping apparatus of FIG. 1.

The motor controller circuitry 38 which governs the operation of the valve stepping motor 34 and the main stepping motor 30 is schematically illustrated in FIG. 2. The circuitry includes a microprocessor 50 connected by a data link 51 to a read-only memory (ROM) 52. Suitable control procedures, including the ramping control procedure of the present invention, for the valve stepping motor 34 and the main stepping motor 30 are stored in the read-only memory 52 and supplied to the microprocessor 50 on demand. The microprocessor, in turn, provides control signals to operate a pair of octal latches 54, 55 to drive the valve stepping motor and the main stepping motor, respectively, in accordance with the control procedures stored in the read-only memory. A pair of sensors 56 and 58 provide a count of the number of steps taken by the valve stepping motor and the main stepping motor, thereby enabling microprocessor 50 to determine the incremental step position of each. A pump runaway prevention circuit 60 is connected to the sensor 56 to monitor the speed of the main stepping motor 30 in order to prevent the occurrence of potentially dangerous fluid over or under delivery conditions as disclosed in prior U.S. Pat. No. 4,470,758 to Vytas V. Pazemenas et al. A multiplexer 62 is connected to various data sensors, such as the plunger pressure transducer (not shown), and an analog-to-digital converter 64 converts the signals from the multiplexer into a form usable by the microprocessor 50, feeding the signals so converted to the microprocessor via data link 65.

Octal latch 54, under the direction of microprocessor 50, is connected to high and low current drivers 70, 71. The high current drivers 70 comprises a set of transistor drivers 72, 73, 74 and 75 respectively connected in series with the motor windings of the main stepping motor 30. The low current drivers 71 comprise a similar set of transistor drivers 76, 77, 78 and 79 respectively connected in series with the motor windings through a set of resistors 80, 81, 82 and 83, respectively. For each incremental step taken by the main stepping motor 30, the octal latch 54 will generate a combination of control signals to switch the high current driver transistors 72-75 on. Thereafter, a relatively large current is drawn from the power control center 44 through the main stepping motor windings to provide sufficient energy for rotating the main stepping motor from one incremental step position to the next position. It will be noted that a relatively high energy level is needed to move the plunger 28 each incremental step, while simultaneously displacing fluid from the pumping chamber 16. On the other hand, a relatively low energy level is required between the incremental steps where the plunger force required is solely that needed to resist the force of the resilient diaphragm 18 tending to return the plunger to its initial uppermost position (FIG. 1). Thus, for the moving portion of the cycle, the high current drivers 70 are switched on from the octal latch 54, while during the low energy holding period between incremental movements the low current drivers 71 are used. These low current drivers 76, 77, 78 and 79 are connected in series with the main stepping motor windings through a set of resistors 80, 81, 82 and 83. A short time after the main stepping motor rotates to its next incremental step position in response to the switching on of high current drivers 72-75, octal latch 54 turns the high current drivers off while simultaneously switching on the low current drivers 76-79. Current is subsequently drawn from power control center 44 through the motor windings and through resistors 80-83 to the low current drivers. The presence of resistors 80-83 reduces the amount of current drawn from power control center 44 to a level sufficient to meet the requirements of the main stepping motor 74 during the motor holding mode; thus, the net amount of energy expended in operating the main stepping motor is conserved.

An analagous arrangement of high current driver transistor and low current driver transistors, shown generally at 90 and 92 respectively, are controlled by an octal latch 55 to energize the valve stepping motor 34 and thereby drive the valve member 22 against a portion of the resilient diaphragm 18 to close off the inlet port 20 during the fluid displacement portion of the pumping cycle.

In the operation of the pumping apparatus of the present invention, the pumping plunger 28 will move from its uppermost position (shown in solid line in FIG. 1) to its lowermost position (shown in phantom line in FIG. 1) to thereby displace a predetermined amount of liquid from chamber 16 in a number of incremental steps. The plunger is then returned at maximum speed to its uppermost position and the process is repeated. The rate of pumping, as set by the user, is determined by the off-time between each incremental pumping step. Furthermore, means are provided for initially pumping at a maximum rate during the initial portion of the plunger cycle as the plunger starts downwardly in order to make up for the lack of fluid delivery during the short time required for the plunger to be retracted from its lowermost position back to its start position. As soon as the volume lost during the plunger retraction period is made up by pumping at the maximum fast rate, the timing of the main stepping motor is such that the increments are timed to achieve the user set rate. Thus, the pump cycle is broken down into a delivery phase, as the plunger 28 descends in the pumping chamber 16 to pump liquid in a plurality of steps, and a refill phase, as the plunger 28 is retracted back to its uppermost starting position and the valve member 22 is lifted to open inlet port 20 and allow the pumping chamber 16 to be refilled with fluid.

Figure 3:
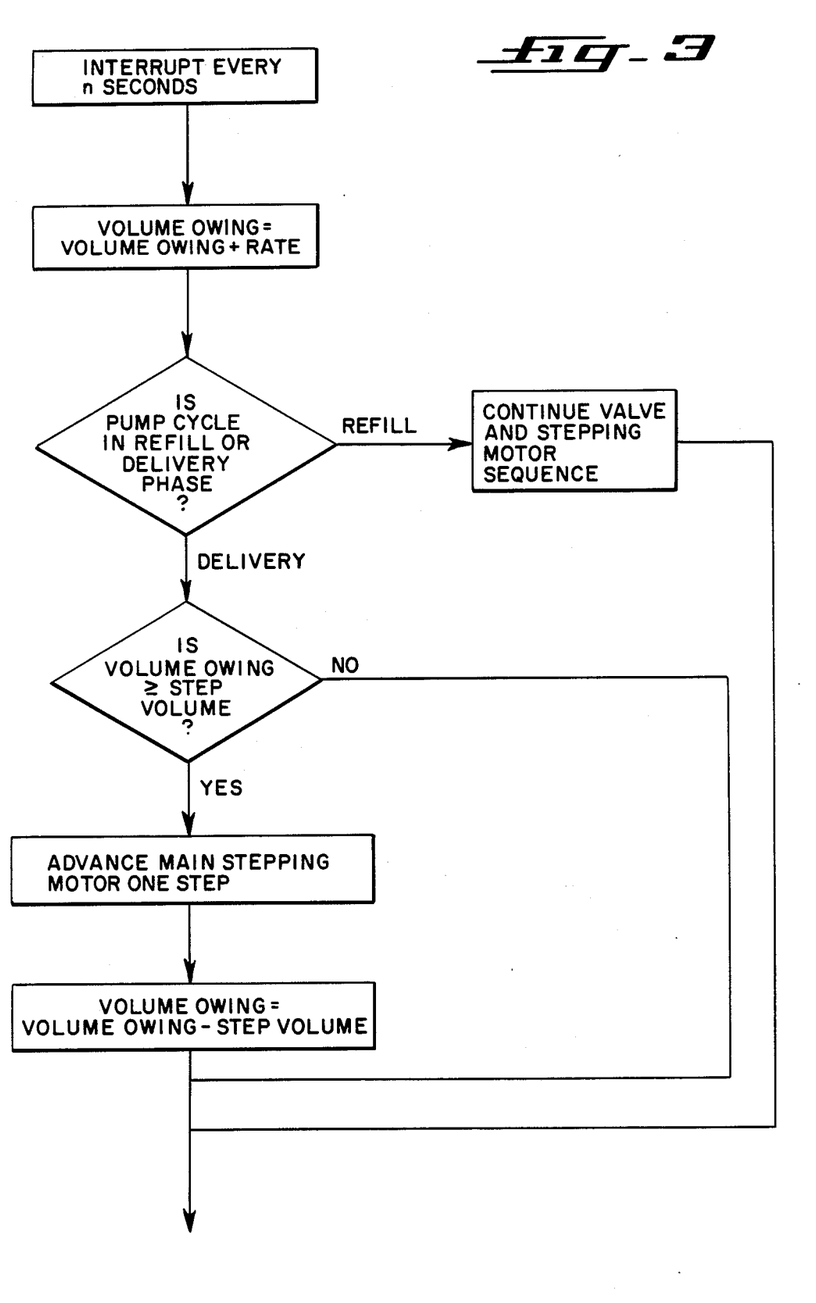
FIG. 3 is a flow chart illustrating the manner in which the microprocessor is programmed to operate the pumping plunger in the apparatus of FIG. 1.

The process by which the microprocessor 50 achieves a nearly uniform flow at the desired user-set rate is outlined in flow chart form in FIG. 3. This process can be visualized essentially as an accounting procedure whereby a running tally is kept of the amount of fluid which should be delivered from the pumping chamber 16 in order to maintain an essentially time-linear average delivery rate at the set rate throughout the pumping cycle. This running tally is then used at the end of the refill phase to drive the main stepping motor 30 at an increased speed until the actual deficit in fluid delivery caused by the refill phase is overcome. At this point, the main stepping motor is driven at the user set rate to provide the essentially constant fluid delivery rate.

As can be seen from FIG. 3, a routine is provided which is interrupted every n seconds, with "n" being a time period which is just long enough to permit the stepping motor 30 to move the plunger 28 from one incremental position to the next. Thus, if the stepping motor is actuated at the update times (i.e., each n seconds) the plunger 28 will be driven at its maximum rate in a continuous, or almost continuous, fashion. A volume owing register in the microprocessor 50 is designated to accumulate rate representative signals (RATE) at the predetermined n second intervals in the pumping cycle. Each RATE signal will be a number directly proportional to the desired fluid delivery rate, i.e., it will be a number proportional to the amount of fluid to be delivered in n seconds in order to equal the user-set rate which is typically provided in mililiters per hour. As seen in FIG. 3, at each update time (n second interval), the RATE signal is added to the number previously accumulated in the volume owing register. A determination is subsequently made as to whether the pumping cycle is in the refill phase or the delivery phase. This determination can be based on the sensed incremental step position of the main stepping motor 30, i.e., if the main stepping motor is at an incremental step position other than those associated with the delivery phase of the pumping cycle, the pumping cycle is in its refill phase. As shown, if the pumping cycle is in the refill phase, the main stepping motor is shifted one increment and the program awaits the next n second interrupt signal. In this manner, the RATE signal is added to the volume owing register every n seconds, and the amount in the volume owing register progressively increases or accumulates throughout the refill phase. When, however, it is determined that the refill phase has ended and the fluid delivery phase has begun, a comparison is made between the accumulated amount in the volume owing register and a predetermined step volume. The step volume represents the average volume of fluid discharged from pumping chamber 16 during each incremental step taken by the main stepping motor 30 during the delivery phase of the pumping cycle. If the amount in the volume owing register is greater than or equal to the value of the step volume, the main stepping motor 30 is advanced one step and the amount in the volume owing register is decreased by the value of the step volume as indicated in FIG. 3. The comparison is then repeated at n second intervals, advancing the main stepping motor 30 through a series of incremental steps to discharge fluid from the pumping chamber 16 at a high delivery rate in the initial portion of the plunger downstroke until the total of fluid so discharged compensates for the interruption in fluid flow which occurs during the refill phase, i.e., until the amount in the volume owning register is depleted to a value less than the value of the step volume representing the volume of fluid discharged from pumping chamber 16 by a single motor step. At this point, and assuming a user-set rate less than the maximum, it will require the addition of a number of RATE signals to the volume owing register (i.e., a number of n second intervals) before the step volume amount is indicated. This situation, wherein the volume of fluid discharged from pumping chamber 16 keeps pace with the amount accumulated in the volume owing register, occurs during the major portion of the delivery phase of each pumping cycle and is characterized by an essentially constant fluid delivery rate.

In accordance with the present invention, the user set rate which determines the value of the RATE signals to be added to the volume owing register in the routine of FIG. 3, will be varied at a number of fractional rates during initial start-up of the pump and will likewise be varied in a series of decreasing fractional rates during the stopping of the pump thereby minimizing physiological shock to the patient. In the preferred embodiment of the invention to be described, the user set rate condition will only be achieved after the pump has pumped for a pre-determined period of time (e.g., one-half hour) at one-third of the user-set rate followed by a pumping period (one-half hour) at two-thirds of the user set rate. Similarly, at a pre-determined time (one hour) prior to the stopping of the pump when the full dosage is delivered, the pump will automatically decrease to a rate two-thirds of the user set rate for a pre-determined period of time (one-half hour) and then switch to a rate one-third of the user set rate until the pump is stopped as the full dosage is delivered (one-half hour later). The user sets the ramping function condition and also sets the total amount or dosage to be delivered as well as the set rate at which the fluid is to be delivered. A series of subroutines, as shown in FIGS. 4, 5 and 6, are then carried out by the microprocessor 50 with each of such subroutines being entered periodically at relatively frequent updating times (e.g., every five miliseconds).

Figure 4:
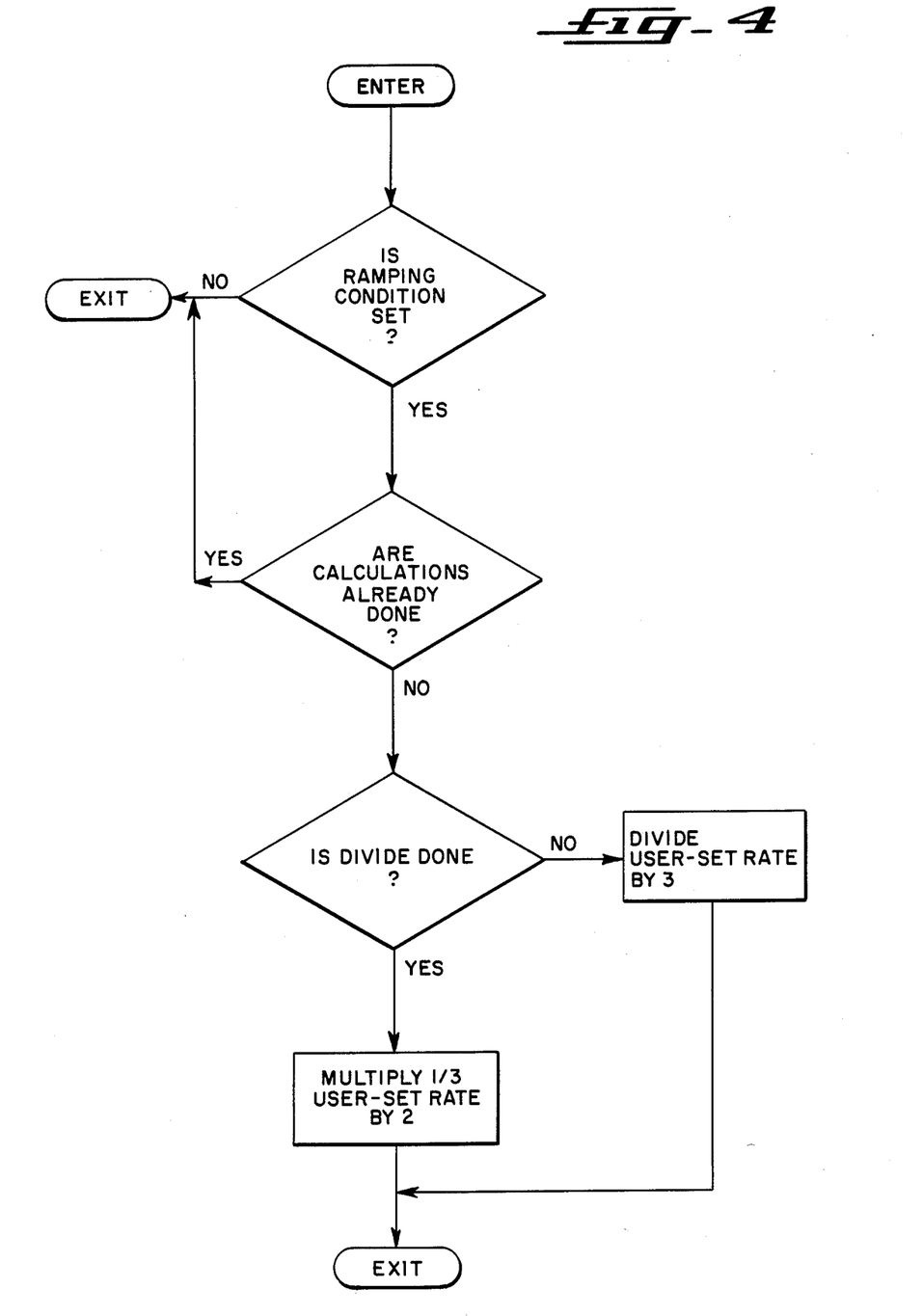
FIG. 4 is a flow chart of the microprocessor subroutine whereby the appropriate calculations are made when the ramping control function of the present invention is utilized with the pumping apparatus of FIG. 1.

Referring now to the microprocessor subroutine of FIG. 4 whereby the calculations for performing the ramping operation are obtained, it will be seen that the program first ascertains whether the ramping condition is set, i.e., whether the ramp function is to be used, and, if not, the program is exited with no further operations being performed. If, on the other hand, the ramping condition is set, the program proceeds to ascertain whether or not the calculations have been done and, if not, the calculations are then carried out in a two-step process, that is to say, it will take two passes through the subroutine of FIG. 4 in order to perform both calculations. As seen, the user-set rate, or maximum pumping rate, is first divided by three to obtain a numbe proportional to one-third of the user rate which will be used in the initial and last portions of the total fluid delivery. On the next pass through the subroutine of FIG. 4, the one-third user set rate is multiplied by two to give a rate proportional to two-thirds of the user set rate which is used between the set rate and the one-third set rate both initially and at the end of the fluid delivery. Once the divide and multiply calculations have been made, appropriate flags are raised and the program is exited as shown in FIG. 4 during subsequent entries without redoing the calculations.

Figure 5:
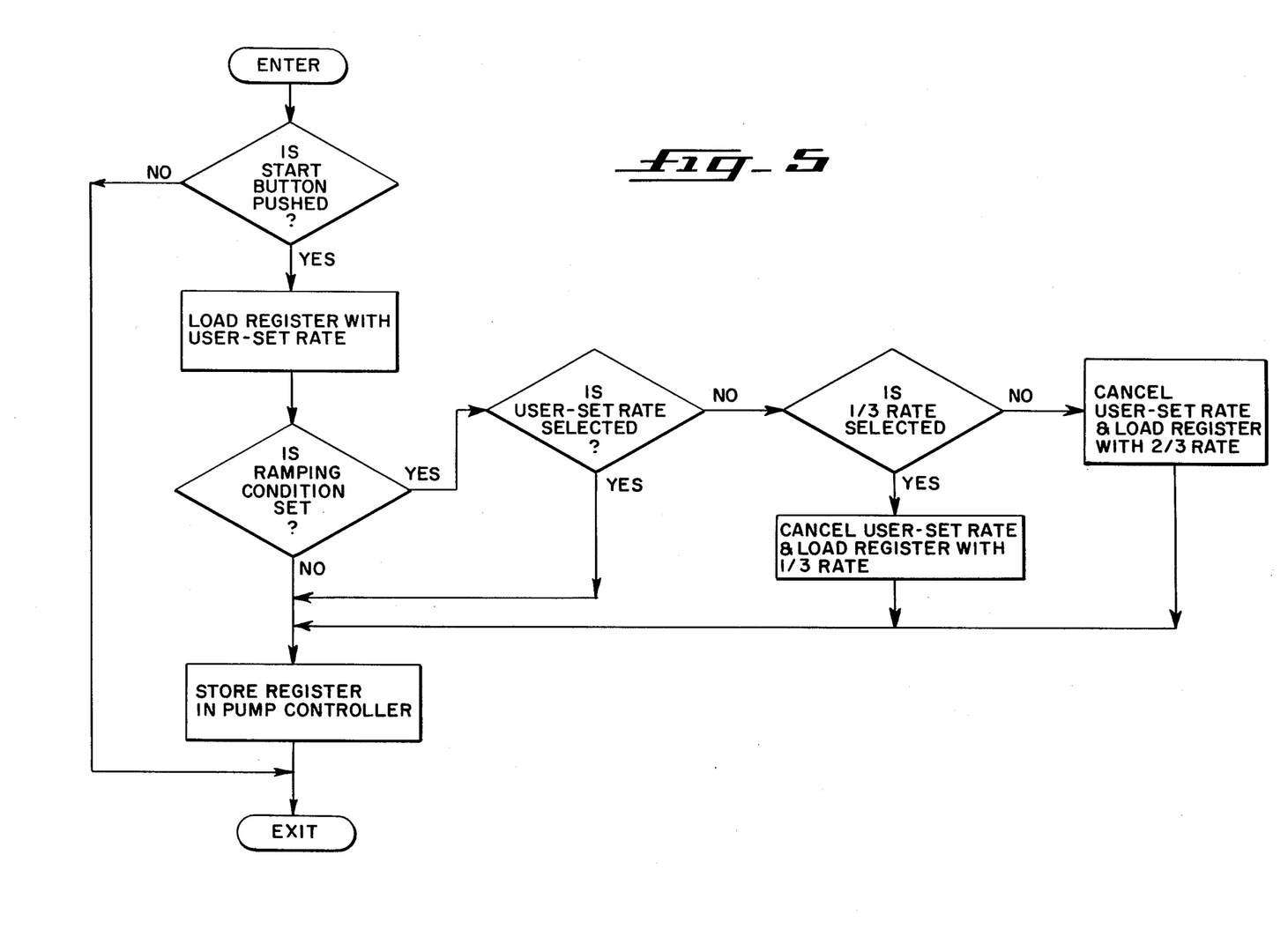
FIG. 5 is a flow chart of the microprocessor subroutine whereby the pumping rates are set when the ramping control function of the present invention is utilized.

The rate setting process performed by the microprocessor processor 50 is shown in FIG. 5. This subroutine is entered at the periodic update rate (5 milliseconds) and is continued if the start button has been pushed to start the pumping operation which program logic decision will remain unchanged and not be reset until the pre-selected total dosage has been delivered to the patient. Continuing with the FIG. 5 subroutine, it will be seen that a register (in the microprocessor) is first loaded with the user-set rate (i.e., the primary or maximum rate of fluid delivery). If the ramping function has not been set, this number will be transferred directly to the pump controller whereby each of the RATE signals (FIG. 3) determining the pump delivery rate will be derived therefrom to perform the pumping operation. If, however, the ramping function is used, the FIG. 5 subroutine monitors the selections made by the rate switching or selection subroutine of FIG. 6 and changes the register loading accordingly. If, for example, at a given time in the pumping of the total dosage the user-set rate has been selected, the program continues in the normal manner with the user-set rate register value simply being stored in the pump controller. If, however, the one-third user-set rate or the two-thirds user-set rate has been selected, the program cancels the user-set rate initially set in the microprocessor register and loads the register with the appropriate one-third or two-thirds rate as provided by the ramp calculation subroutine of FIG. 4. This new rate then becomes the rate which is transferred to the pump controller and from which the RATE signals are derived during the incremental stepping of the motor 30.

Figure 6:
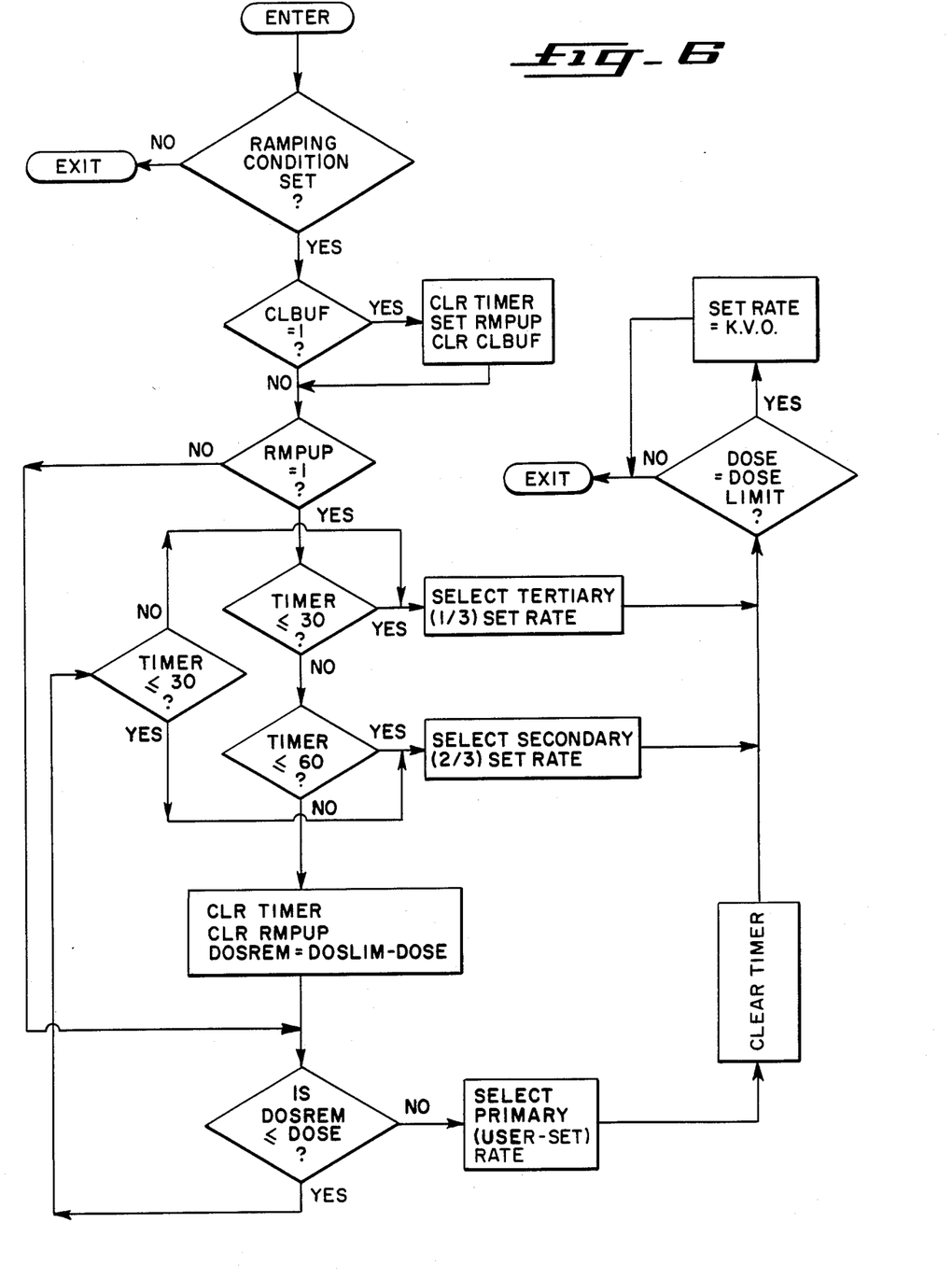
FIG. 6 is a flow chart of the microprocessor subroutine for performing the switching between pumping rates when the ramping control function of the present invention is utilized.

The means whereby the selections are made for the rate setting subroutine of FIG. 5 are provided by the rate switching subroutine of FIG. 6. This subroutine is entered and exited if the ramping condition is not set but with the program continuing if the ramping condition is set. A buffer clear enable flag (CLBUF) will have been set to a logic "one" at the time when the ramping conditions are intially set. As can be seen from FIG. 6, this permits the program, on the first pass through only, to set the ramping up flag (RMPUP) to indicate the upramping condition at the start of the pumping cycle and to also clear the minute timer (TIMER) so that it can initiate a timing sequence. The CLBUF bit is simultaneously cleared or set to a logic "zero" state, so that this block of setting and clearing functions are not accessed again during the delivery of the pre-set dose. With the ramping up flag set at a logic "one", the program looks for a 30-minute count on the minute timer, and, since the timer will indicate less than 30 minutes for the initial entry and for all subsequent entries through the next 30 minutes, the program will select the tertiary or one-third user-set rate as the selected running speed, determine that the dose delivered thus far is less than the dose limit (i.e., total dosage), and exit. This will continue until the end of a 30-minute time period wherein the logic decision is made indicating that at least 30 minutes have passed but less than 60 minutes have passed as set by the minute timer. As seen, this will then cause the program to select the secondary or two-thirds user-set rate as the running speed before exiting. Upon the arrival of the 60-minute time lapse since the start of pumping, the minute timer will be cleared and the ramping-up flag (RMPUP) will be set to zero in preparation for the ramping-down phase at the end of the delivery cycle. In addition, the dose remaining to be delivered (DOSREM) is computed by substracting from the total dosage or dose limit (DOSLIM) the accumulated running total dose actually delivered thus far (DOSE). This calculation, which will be performed only once during the total delivery cycle, is stored and thereafter sequentially compared with the accumulated dose (DOSE) to determine when to start the ramping-down cycle one hour from the end of the delivery. As will be appreciated, if one-half or more of the total dose to be delivered has been delivered at the time that the rampingup portion of the cycle has been completed, the program will immediately switch to the ramping-down function whereby the minute clock will begin timing and the secondary or two-thirds set rate will be selected. After 30 minutes, the programming will select the tertiary or one-third set rate which will continue until the total dose (DOSE) equals the dose limit, at which point the rate is set to a K.V.O. (keep-vein-open) rate which is a very low rate (e.g., 4 ml/hr), just enough to keep the vein entry site from clotting. If, on the other hand, at the conclusion of the ramping-up function, less than half of the total dose has been delivered (which will be the usual condition) then the dose remaining number stored in the register (DOSREM) will be greater than the total dose delivered and the primary or user set rate will be selected with the minute timer being cleared at each subsequent reentry of the subroutine. This procedure will be continued until DOSREM equals or is less than the total dose delivered. It will be appreciated that this equality will occur at a point when the total dose delivered upon the calculation and storing of DOSREM is exactly equal to the remaining dose to be delivered (i.e., the amount delivered during the first hour exactly equals the amount which is to be delivered during the last hour of the total dose delivery). At this point, the logic function switches to the 30-minute timing function with first the secondary rate being employed and then the tertiary rate being employed after another 30 minutes all as aforedescribed.

It will thus be seen that the circuitry and software of the present invention provides an automatic means for infusing fluids, and particularly dangerous drugs, to a patient in a carefully programmed manner so that the dosage is gradually increased to a pre-set delivery rate at the beginning of the pumping cycle and wherein the delivery rate is gradually decreased at the end of the pumping cycle so as to minimize physiological shocks to the patient.

Although the best mode contemplated for carrying out the present invention has been herein shown and described, it will be apparent that modification and variation can be made without departing from what is regarded to be the subject matter of the invention.

What is claimed is:

1. In an infusion pumping apparatus having a motor for driving a pumping member to expel liquid, from a pumping chamber having an input from a single source of said liquid, at a rate as determined by a preset motor output rate, ramping control means for initiating the pumping of said liquid by operating the motor at a plurality of starting fractional rates for predetermined periods of time until the preset rate is obtained, each starting fractional rate being less than the preset rate and successive starting fractional rates increasing the motor rate, maintaining said preset rate for a selected period of time and means for stopping the motor after a predetermined quantity of said liquid has been delivered, said ramping control means also operating the motor at a plurality of stopping fractional rates for predetermined periods of time prior to the stopping of the motor, each stopping fractional rate being less than the preset rate and successive stopping fractional rates decreasing the motor speed.

2. In an infusion pumping apparatus according to claim 1 including means for timing said starting and stopping fractional rates, and means for starting said timing means upon the initiation of pumping and upon the initiation of the stopping fractional rate pumping periods.

3. In an infusion pumping apparatus according to claim 1 wherein said ramping control means includes means for computing and storing a figure corresponding to the dose remaining by subtracting the total accumulated amount of said liquid delivered at the conclusion of the starting fractional rate pumping periods from said predetermined quantity of said liquid to be delivered, and means for thereafter sequentially comparing said figure with the accumulated amount of said liquid delivered and for initiating said stopping fractional rate pumping periods when the accumulated amount is equal to or greater than said figure.

4. In an infusion pumping apparatus according to claim 3 including means for timing said starting and stopping fractional rate pumping periods, means for starting and stopping fractional rate pumping periods, means for starting said timing means upon the initiation of pumping, and means for periodically resetting the timing means after said starting fractional rate pumping periods and until the initiation of said stopping fractional rate pumping periods.

5. In an infusion pumping apparatus according to claim 1 wherein the total time for said starting fractional rate pumping periods is in the order of one hour and wherein the total time for said stopping fractional rate pumping periods is in the order of one hour.

6. In an infusion pumping apparatus according to claim 5 wherein there are two starting fractional rates and two stopping fractional rates, said fractional rates being approximately one-third and two-thirds of said preset motor output rate.

7. An infusion pumping apparatus comprising a motor, a pumping chamber having an input from a single source of liquid, a pumping member operatively connected to said motor and arranged to expel said liquid from the pumping chamber at a rate as determined by a preset motor output rate, means for initiating the operation of said motor, ramping control means operative upon the initiation of said last named means for operating the motor at a plurality of starting fractional rates for predetermined periods of time until the preset rate is obtained, each starting fractional rate being less than the preset rate and successive starting fractional rates increasing the motor speed, maintaining said preset rate for a selected period of time, and means for stopping the motor after a predetermined quantity of said liquid has been delivered, said ramping control means also operating the motor at a plurality of stopping fractional rates for predetermined periods of time prior to the stopping of the motor, each stopping fractional rate being less than the preset rate and successive stopping fractional rates decreasing the motor speed.

8. An infusion pumping apparatus according to claim 7 including means for timing said starting and stopping fractional rates, and means for starting said timing means upon the initiation of pumping and upon the initiation of the stopping fractional rate pumping periods.

9. An infusion pumping apparatus according to claim 7 wherein the total time for said starting fractional rate pumping periods is in the order of one hour and wherein the total time for said stopping fractional rate pumping periods is in the order of one hour.

10. An infusion pumping apparatus according to claim 7 wherein there are two starting fractional rates and two stopping fractional rates, said fractional rates being approximately one-third and two-thirds of said preset motor output rate.

11. An infusion pumping apparatus according to claim 7 wherein said pumping member is operated by said motor in a plurality of sequential steps during a single stroke thereof to expel said liquid from the pumping chamber, said motor output rate being determined by the time between each of said steps, means for storing a step volume value equivalent to the amount of said liquid to be delivered during one motor step, means for periodically comparing said step volume value with an accumulated total of rate signals between each step, said rate signals being provided by said ramping control means, and means for advancing said motor by one step when the accumulated rate signal total equals the step volume value.

12. An infusion pumping apparatus according to claim 7 wherein said ramping control means includes means for computing and storing a figure corresponding to the dose remaining by subtracting the total accumulated amount of said liquid delivered at the conclusion of the starting fractional rate pumping periods from said predetermined quantity of said liquid to be delivered, and means for thereafter sequentially comparing said figure with the accumulated amount of said liquid delivered and for initiating said stopping stopping fractional rate pumping periods when the accumulated amount is equal to or greater than said figure.

13. An infusion pumping apparatus according to claim 12 including means for timing said starting and stopping fractional rate pumping periods, means for starting said timing means upon the initiation of pumping, and means for periodically resetting the timing means after said starting fractional rate pumping periods and until the initiation of said stopping fractional rate pumping periods.

* * * * *